(12) United States Patent
Matsumoto et al.

(10) Patent No.: US 9,434,965 B2
(45) Date of Patent: Sep. 6, 2016

(54) PRODUCTION METHOD FOR ORGANIC ACID USING COA-TRANSFERASE

(71) Applicants: SHOWA DENKO K.K., Minato-ku, Tokyo (JP); NATIONAL UNIVERSITY CORPORATION HOKKAIDO UNIVERSITY, Sapporo-shi, Hokkaido (JP)

(72) Inventors: Ken'ichiro Matsumoto, Sapporo (JP); Seiichi Taguchi, Sapporo (JP); Hirobumi Aoki, Kawasaki (JP)

(73) Assignees: SHOWA DENKO K.K., Tokyo (JP); NATIONAL UNIVERSITY CORPORATION HOKKAIDO UNIVERSITY, Sapporo-shi (JP)

( * ) Notice: Subject to any disclaimer, the term of this patent is extended or adjusted under 35 U.S.C. 154(b) by 0 days.

(21) Appl. No.: 14/351,497

(22) PCT Filed: Oct. 10, 2012

(86) PCT No.: PCT/JP2012/076194
§ 371 (c)(1),
(2) Date: Apr. 11, 2014

(87) PCT Pub. No.: WO2013/058150
PCT Pub. Date: Apr. 25, 2013

(65) Prior Publication Data
US 2014/0234927 A1 Aug. 21, 2014

(30) Foreign Application Priority Data

Oct. 18, 2011  (JP) .................................. 2011-228751
Mar. 21, 2012  (JP) .................................. 2012-063097

(51) Int. Cl.
C12P 7/42 (2006.01)
(52) U.S. Cl.
CPC ...................................... *C12P 7/42* (2013.01)
(58) Field of Classification Search
None
See application file for complete search history.

(56) References Cited

FOREIGN PATENT DOCUMENTS

WO 2010/023206 A1 3/2010

OTHER PUBLICATIONS

Extended European Search Report dated Jun. 16, 2015, issued by the European Patent Office in counterpart European application No. 12841518.9.
Duncan et al: "Acetate utilization and butyryl coenzyme A (CoA): acetate-CoA transferase in butyrate-producing bacteria from the human large intestine", Applied and Environmental Microbiology, vol. 68, 2002, pp. 5186-5190, XP002740509.
Yamada et al: "Adjustable mutations in lactate (LA)—polymerizing enzyme for the microbial production of LA-based polyesters with tailor-made monomer composition", Biomacromolecules, vol. 11, 2010, pp. 815-819, XP002740510.
Qian Liu et al., "Microbial production of R-3-hydroxybutyric acid by recombinant *E. coli* harboring genes of phbA, phbB, and tesB", Appl. Microbiol. Biotechnol., 2007, pp. 811-818, vol. 76, No. 4.
Hai-Jun Gao et al., "Enhanced production of D-(-)-3-hydroxybutyric acid by recombinant *Escherichia coli*", FEMS Microbiology Letters, 2002, pp. 59-65, vol. 213, No. 1.
Ralf Jossek et al., "In vitro synthesis of poly(3-hydroxybutyric acid) by using an enzymatic coenzyme A recycling system", FEMS Microbiology Letters, 1998, pp. 319-324, vol. 168 No. 2.
Ken'Ichiro Matsumoto et al., "Efficient (R)-3-hydroxybutyrate production using acetyl CoA-regenerating pathway catalyzed by coenzyme A transferase", Appl. Microbiol. Biotechnol., 2013, pp. 205-210, vol. 97 No. 1.
Toshihiko Ooi et al., "Production of 3-hydroxybutyric acid using CoA transferase", Dai 64 Kai Abstracts of the Annual Meeting of the Society for Biotechnology, Sep. 25, 2012, pp. 26, vol. 64, 2Ba12.
Toshihiko Ooi et al., "Production of 3-hydroxybutyric acid using CoA transferase"; Dai 64 Kai Abstracts of the Annual Meeting of the Society for Biotechnology; Sep. 25, 2012; vol. 64; 2Ba12; pp. 26.
Buenaventurada P. Calabia et al.; "Microbial degradation of poly(D-3-hydroxybutyrate) by a new thermophilic Streptomyces isolate"; Biotechnology Letters 26; 2004; pp. 15-19.
Sang Yup Lee et al; Metabolic Engineering of *Escherichia coli* for Production of Enantiomerically Pure (R)-(-)-Hydroxycarboxylic Acids; Applied and Environmental Microbiology; vol. 69; No. 6; Jun. 2003; pp. 3421-3426.
Hsien-Chung Tseng, et al; Metabolic Engineering of *Escherichia coli* for Enhanced Production of (R)- and (S)-3-Hydroxybutyrate; Applied and Environmental Microbiology; vol. 75, No. 10; May 2009; pp. 3137-3145.

*Primary Examiner* — Suzanne M Noakes
(74) *Attorney, Agent, or Firm* — Sughrue Mion, PLLC

(57) ABSTRACT

The present invention relates to a method of producing organic acids, comprising biochemical synthesis of organic acid-CoA using acetyl-CoA as a substrate and conducting CoA elimination reaction of the organic acid-CoA using CoA transferase in the presence of acetic acid, in which organic acid is obtained by culturing transformed microorganisms which have an enzyme gene cluster for the synthesis of organic acid-CoA using acetyl-CoA as a substrate and a CoA transferase gene.

9 Claims, 2 Drawing Sheets

PRODUCTION METHOD FOR ORGANIC ACID USING COA-TRANSFERASE

CROSS REFERENCE TO RELATED APPLICATIONS

This application is a National Stage of International Application No. PCT/JP2012/076194 filed Oct. 10, 2012, claiming priority based on Japanese Patent Application No. 2011-228751 filed Oct. 18, 2011 and 2012-063097 filed Mar. 21, 2012, the contents of all of which are incorporated herein by reference in their entirety.

TECHNICAL FIELD

The present invention relates to a biochemical method of producing organic acids using CoA transferase. Specifically, the present invention relates to a biochemical method of producing organic acids, which is excellent in carbon yield and energy efficiency, by using transformed microorganisms which produces a CoA transferase serving as a catalyst of CoA elimination reaction of the organic acid-CoA.

BACKGROUND ART

Recently, from the viewpoint of depletion of fossil resources and measures against global warming, a shift to a manufacturing process of chemical goods using renewable resources (so-called bio-refinery) has been required. In particular, the application of various organic acids which can be efficiently obtained biochemically from biomass has been widely studied as the next-generation chemical block. For example, hydroxycarboxylic acids are a useful compound not only as a synthesis material of fine organic chemicals but also as a monomer unit of polyhydroxyalkanoic acid (PHA), as a bio-polyester which is known as being produced by the accumulation in microorganisms. In particular, poly-3-hydroxybutanoic acid which is a typical PHA derived from microorganisms attracted attention to its property as a biodegradable polymer mainly in 1980-1990's and a vigorous attempt has been made for the elucidation of the biosynthetic pathway and the productivity improvement. Recently, the potential of 3-hydroxybutanoic acid being a structure unit of poly-3-hydroxybutanoic acid as a chemical block has been attracting attention again, and various biochemical methods of producing a 3-hydroxybutanoic acid monomer have been proposed.

Specifically, the methods as follows are known:
  a method of extracting poly-3-hydroxybutanoic acid accumulated in the microbial cell body and hydrolyzing it by the action of the enzyme or microorganism having degradation activity to obtain (R)-3-hydroxybutanoic acid as being a monomer unit (Non-patent Document 1);
  a method of allowing high expression in vivo of poly-3-hydroxybutanoic acid depolymerase in poly-3-hydroxybutanoic acid-producing bacteria and sequentially degrading the generated 3-hydroxybutanoic acid oligomer to obtain (R)-3-hydroxybutanoic acid during the culture period (Non-patent Document 2);
  a method of eliminating CoA by the conjugate with phosphorylation by allowing coexpressed phosphotrans butyrylase (ptb) and butyrate kinase (buk) to act sequentially on 3-hydroxybutyryl CoA in vivo as being a precursor of 3-hydroxybutanoic acid to obtain (R)-3-hydroxybutanoic acid during the culture period (Non-patent Document 3); and
  a method of eliminating CoA by allowing coexpressed thiolase to act sequentially on 3-hydroxybutyryl CoA to obtain (R)-3-hydroxybutanoic acid during the culture period (Non-patent Document 4).

PRIOR ART

Non-Patent Document

Non-patent Document 1: Calabia, B. P., Tokiwa, Y., 2004. Microbial degradation of poly(d-3-hydroxybutyrate) by a new thermophilic Strepromyces isolate. Biotechnol. Lett. 26, 15-19.

Non-patent Document 2: Lee, S. Y., Lee, Y., 2003. Metabolic engineering of *Escherichia coli* for production of enantiomerically pure (R)-(−)-hydroxycarboxylic acids. Appl. Environ. Microbiol. 69, 3421-3426.

Non-patent Document 3: Gao, H. J., Wu, Q., Chen, G. Q., 2002. Enhanced production of d-(−)-3-hydroxybutyric acid by recombinant *Escherichia coli*. FEMS microbiol. Lett. 213, 59-65.

Non-patent Document 4: Tseng et al., "Metabolic Engineering of *E. coli* for Enhanced Production of (R)- and (S)-3-Hydroxybutyrate", 2009, Appl. Environ. Microbiol., 75, 3137-3145.

DISCLOSURE OF THE INVENTION

Problems to be Solved by the Invention

However, the economic sufficiency is not enough in these proposed methods and further improvement in productivity has been demanded. For example, the method of Non-patent Document 1 requires cumbersome processes of fermentation, extraction and degradation. In the method of Non-patent Document 2, the production rate is low because poly-3-hydroxybutanoic acid is produced by anaerobic fermentation and subjected to hydrolysis. In the methods of Non-patent Documents 3 and 4, the productivity of 3-hydroxybutanoic acid is not enough due to the low carbon yield.

Accordingly, an objective of the present invention is to provide a biochemical method of producing organic acids, 3-hydroxybutanoic acid monomer in particular, which is excellent in the production rate, carbon yield and energy efficiency.

Means to Solve the Problem

The present inventors have closely investigated in the finding described in the above-mentioned Non-patent Documents 1 to 4 and have made an extensive study aiming for substantive increase in the reaction efficiency in the biosynthesis path of organic acids by the conjugate with CoA. As a result, the present inventors have found that the productivity of organic acids can be improved efficiently by biochemical synthesis of organic acid CoA at least by using acetyl CoA as a substrate and conducting CoA elimination reaction of the above-mentioned organic acid CoA with CoA transferase in the presence of acetic acid added to the reaction system; and have accomplished the present invention.

That is, the present invention relates to the method of organic acid as described in [1] to [9] as below.

[1] A method of producing organic acids, comprising biochemical synthesis of organic acid-CoA using acetyl-CoA as a substrate and conducting CoA elimination reaction of the organic acid-CoA using CoA transferase in the presence of acetic acid.

[2] The method of producing organic acids as described in [1] above, wherein the CoA transferase is propionic acid-CoA transferase or a homologue thereof.

[3] The method of producing organic acids as described in [1] or [2] above, wherein the organic acid is carboxylic acid having 3 to 6 carbon atoms.

[4] The method of producing organic acids as described in [3] above, wherein the organic acid is hydroxycarboxylic acid having 3 to 6 carbon atoms.

[5] The method of producing organic acids as described in [4] above, wherein the organic acid is 3-hydroxypropionic acid, 3-hydroxybutanoic acid, 3-hydroxyvaleric acid or 3-hydroxyhexanoic acid.

[6] The method of producing organic acids as described in any one of [1] to [5] above, in which organic acid is obtained by culturing transformed microorganisms which have an enzyme gene cluster for the synthesis of organic acid-CoA using acetyl-CoA as a substrate and a CoA transferase gene in the presence of acetic acid.

[7] The method of producing organic acids as described in [6] above, in which 3-hydroxybutanoic acid is obtained by culturing transformed microorganisms which have an enzyme gene cluster for the synthesis of 3-hydroxybutyryl CoA using acetyl-CoA as a substrate and a CoA transferase gene in the presence of acetic acid.

[8] The method of producing organic acids as described in [7] above, in which the enzyme gene cluster for the synthesis of 3-hydroxybutyryl CoA is β-ketothiolase gene or a homologue thereof, or acetoacetyl-CoA reductase gene or a homologue thereof; and the CoA transferase is a propionic acid-CoA transferase gene (PCT) or a homologue thereof.

[9] The method of producing organic acids as described in any one of [6] to [8] above, wherein the microorganism is *Escherichia coli*, yeast, *Corynebacterium* or *Clostridium*.

Effects of the Invention

In methods of producing various organic acids involving CoA elimination of organic acid-CoA obtained by biochemical synthesis at least using acetyl-CoA as a substrate, the present invention is to provide a method of producing organic acids using CoA transfer reaction of acetic acid which conjugates with the CoA elimination of organic acids in the presence of acetic acid added to the reaction system.

According to the present invention, in the biochemical synthesis path of organic acids by the conjugate with CoA, free energy of organic acid-CoA as being an active intermediate is collected as acetyl-CoA through the CoA transfer reaction by the conjugate with acetic acid present in the reaction system. The generated acetyl-CoA is equivalent to the acetyl-CoA as being a material of the biochemical synthesis of organic acids, and is taken again in the biochemical synthesis path of organic acids; and the free energy of the acetyl-CoA is reutilized for the carbon skeleton elongation reaction. The acetic acid per se supplied during the process is utilized as the carbon skeleton source in the biochemical synthesis path of organic acids, and the biochemical synthesis of organic acids can be achieved which is excellent in any of the production rate, energy efficiency and carbon yield without causing material loss.

In the method of the present invention, it is essential to perform the reaction in the presence of acetic acid added to the reaction system. It is generally known that many of microorganisms exhaust acetic acid as a by-product during the proliferative process using carbohydrates and the like. In the present invention, acetic acid obtained as a bi-product is used as a donor in the CoA transfer in the synthesis of target organic acids, and the acetyl-CoA generated in the transfer reaction is used for a carbon skeleton in the synthesis of organic acids, which contribute to effective use for the target reaction of the medium carbon source.

Figure 3:
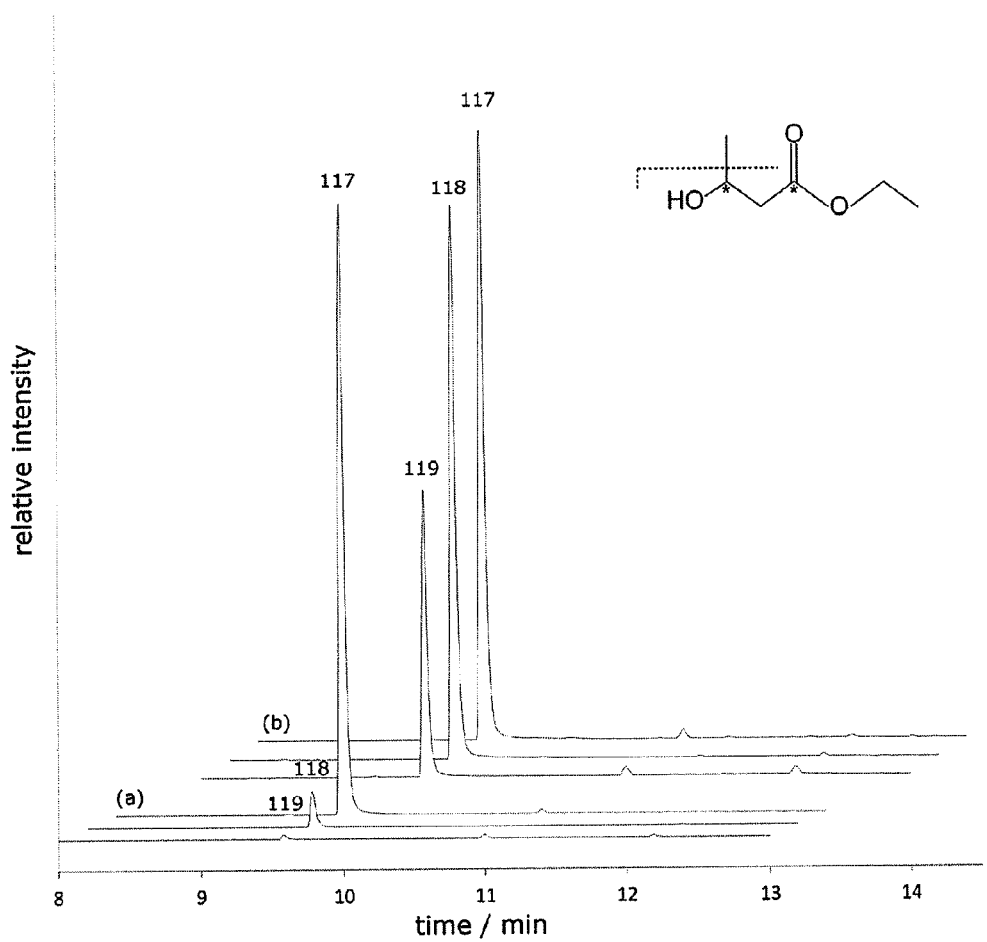
FIG. 3 are GC/MS chromatograms of Examples 5 and 8.

(a) 3-hydroxybutanoic acid ethyl ester derived from Example 5 produced in the presence of non-labeled acetic acid (b) 3-hydroxybutanoic acid ethyl ester derived from Example 8 produced in the presence of acetic acid labeled with $^{13}C$ In the structure formula of 3-hydroxybutanoic acid ethyl shown in the upper right of FIG. 3, * indicates carbon which can be labeled with $^{13}C$.

MODE FOR CARRYING OUT THE INVENTION

There is no particular limit on the organic acids as the synthesis target in the method of the present invention as long as the organic acid allows obtaining organic acid-CoA as a precursor by the reaction which at least uses acetyl-CoA as a substrate, and the organic acid-CoA can become a substrate of the transferase used in the CoA elimination in conjugate with acetic acid. From the view point of the substrate specificity of the generally known CoA transferase, the organic acid is preferably carboxylic acid having 3 to 6 carbon atoms, and more preferably, hydroxycarboxylic acid having 3 to 6 carbon atoms. Specifically, example of the organic acid include 3-hydroxypropionic acid, 3-hydroxybutanoic acid, 3-hydroxyvaleric acid and 3-hydroxyhexanoic acid.

The reaction path and group of enzymes for supplying organic acid-CoA, by using acetyl-CoA as a substrate, as a precursor toward the CoA elimination by the conjugate with acetic acid can be arbitrarily selected depending on the target organic acid. For example, in the reaction process targeting 3-hydroxybutanoic acid, the reaction to obtain 3-hydroxybutyryl CoA as a precursor for the CoA elimination in conjugate with acetic acid is attained by the two-stage combination of enzyme reaction of β-ketothiolase (EC: 2.3.1.9) or a homologue thereof to synthesize acetoacetyl CoA from two molecular-acetyl CoA involving elimination of one molecular CoA; and acetoacetyl-CoA reductase or a homologue thereof to reduce the generated acetoacetyl CoA and synthesize 3-hydroxybutyryl-CoA. In the description and scope of claims of the present invention, the acetoacetyl-CoA reductase includes not only the enzyme named acetoacetyl-CoA reductase (EC: 1.1.1.36; producing (R)-3-hydroxybutyryl-CoA) but also 3-hydroxybutyryl CoA dehydrogenase (EC: 1.1.1.35; producing (S)-3-hydroxybutyryl-CoA), 3-hydroxyacyl CoA dehydrogenase (EC: 1.1.1.157; producing (S)-3-hydroxybutyryl-CoA) and the like unless otherwise noted.

The transferase for the CoA elimination in conjugate with acetic acid used in the present invention can be arbitrarily selected depending on the target organic acid. For example, in the reaction process targeting 3-hydroxybutanoic acid, propionic acid-CoA transferase (EC: 2.8.3.1) or a homologue thereof can be used.

The optical selectivity of the organic acid obtained by the present invention depends on the optical selectivity of the organic acid-CoA obtained as mentioned above, or the optical selectivity of the enzyme reaction arbitrarily selected in the biochemical synthesis path of the organic acid-CoA. The adoption of the CoA transferase reaction has no affect on the optical selectivity of the organic acid. That is, the present invention can be applied for producing any desired optically-active substance by appropriately selecting the chirality of the reaction path to obtain the organic acid-CoA as a precursor. For example, propionic acid-CoA transferase (PCT) selected as an example in the reaction process targeting 3-hydroxybutanoic acid can perform CoA transfer using acetic acid as an acceptor on either of (S)-isomoer or (R)-isomer of 3-hydroxybutyryl CoA. Chiral 3-hydroxybutanoic acid can be obtained by appropriately selecting the optical selectivity of 3-hydroxybutyryl CoA as a precursor thereof or that of the enzyme employed in the production path of 3-hydroxybutyryl CoA. For example, it is known that from acetoacetyl-CoA, (R)-3-hydroxybutyryl CoA can be obtained by using acetoacetyl-CoA reductase (PhaB) derived from microorganisms belonging to *Ralstonia* genus; and (S)-3-hydroxybutyryl CoA can be obtained by using acetoacetyl CoA reductase (hbd) derived from microorganisms belonging to *Clostridium* genus. By combining the above-mentioned processes with the CoA transferase in conjugate with acetic acid of the present invention, (R)-3-hydroxybutanoic acid and (S)-3-hydroxybutanoic acid can be obtained, respectively.

In one suitable embodiment to carry out the present invention, a series of enzyme cluster selected depending on the desired organic acid as mentioned above is coexpressed in the cell of microorganisms transformed by genetic modification. For example, in the production of 3-hydroxybutanoic acid, a gene which codes each of above-mentioned enzymes: i.e. β-ketothiolase (EC: 2.3.1.9) or a homologue thereof, acetoacetyl-CoA reductase (EC: 1.1.1.35, EC: 1.1.1.36, EC: 1.1.1.157) or a homologue thereof and propionic acid-CoA transferase (EC: 2.8.3.1) or a homologue thereof; is inserted in an arbitrary vector respectively or as a series of cluster to transform the host microorganism. A transformant thus obtained is cultured in a medium containing an appropriate carbon source such as glucose, for example, to express each gene. For example, each coding gene is expressed as it is if the gene is the one which can be constituted and expressed by the host; or expressed by addition of an inducing substrate or transfer to an inducing environment if the gene is constituted under the control of the regulator arranged on the vector. Furthermore, a series of reactions proceed, which employs the acetyl-CoA supplied by the glycolysis system of the host as a reaction material, by allowing acetic acid which comes to be a substrate in the CoA transfer reaction in conjugate with acetic acid, and the synthesis of 3-hydroxybutanoic acid as one objective of the present invention can be achieved with high efficiency.

Examples of the genes which code each enzyme used in the present invention includes β-ketothiolase (PhaA) gene derived from microorganisms belonging to *Ralstonia* genus, acetoacetyl-CoA reductase (PhasB) gene derived from microorganisms belonging to *Ralstonia* genus and propionic acid-CoA transferase (PCT) genes derived from microorganisms belonging to *Megasphaera* genus or *Clostridium* genus. There is no particular limit on the transformed host microorganisms used in the present invention as long as genetic recombination technology can be applied to the microorganism. Examples of the microorganisms which are suitable for industrial use include *Escherichia coli*, yeast, *Corynebacterium* and bacteria belonging to *Clostridium* genus. Examples of the yeast include *Saccharomyces cerevisiae*, *Schizosaccharomyces pombe*, *Kluyveromyces lactis* and *Kluyveromyces marxianus*. Examples of *Corynebacterium* include *Corynebacterium glutamicum*, *Corynebacterium efficiens*, *Brevibacterium divaricatum*, *Brevibacterium saccharolyticum*, *Brevibacterium immariophilum*, *Brevibacterium lactofermentum*, *Brevibacterium roseum*, *Brevibacterium flavum*, *Brevibacterium tiogenitalis*, *Corynebacterium acetoacidophilum*, *Corynebacterium acetoglutamicum*, *Corynebacterium callunae*, *Corynebacterium lilium*, *Corynebacterium melassecola* and *Microbacterium ammoniaphilum*. Examples of bacteria belonging to *Clostridium* genus include *Clostridium kluyveri*, *Clostridium acetobutylicum*, *Clostridium aminobutyricum*, *Clostridium beijerinckii* and *Clostridium saccharoperbutylacetonicum*. Among these, *Escherichia coli*, *Saccharomyces Cerevisiae*, *Shizosaccharomyces pombe*, *Corynebacterium glutamicum* are suitably used due to the easiness of transformation, and *Escherichia coli* is particularly preferable. Beginning with acetyl-CoA, not all the enzyme genes which constitute the target biosynthesis paths have to be supplied as foreign genes by the transformation, but the biosynthesis path may be constituted by utilizing the enzyme genes inherent to the host in portion of the path. Furthermore, with respect to the acetyl-CoA supply, not only using the metabolic pathway of the host as it is, but the acetyl-CoA obtained by improving supplying capability by using known metabolic engineering methods such as gene amplification, introduction of foreign genes and knockout of branch paths can be used as well.

The word "homologue" referred to in the present invention encompasses ortholog and paralog. In the present specification, the ortholog refers to corresponding genes between species developed from the common ancestor by species differentiation, and enzymes obtained by the genes. The paralog refers to corresponding genes in the same species arisen not through the species differentiation but through gene duplication, and a pair of enzymes obtained from the genes. The homologue means the genes having homologous sequences regardless of being an ortholog or a paralog and the enzymes obtained by the genes. These homologues can be obtained as genes or enzymes obtained through the transformation of the genes by applying a homology search program (BLAST, FASTA and the like) to appropriate database, or using conventional means such as hybridization and PCR using a probe made by all or part of the above identified genes.

In the present invention, acetyl-CoA which comes to be a substrate in the synthesis of organic acid-CoA is preferably supplied from an arbitrary carbon source used for the cultivation, for example, derived from carbohydrate such as glucose by the glycolysis system of the host in the production by the recombinant as mentioned above. Acetyl-CoA is also supplied at the same time as the acetyl-CoA derived from the acetic acid, which is added as a conjugate substrate in the CoA transfer in conjugate with acetic acid in the synthesis path of organic acid, and generated with the progress of the reaction. That is, in addition to the carbon source such as carbohydrate as a material of the cultivation or reaction, the acetic acid added in the reaction is not only consumed as the conjugate substrate in the CoA transfer reaction of the organic acid-CoA, but also is collected as a synthesis substrate of the target organic acid and a free energy source for the synthesis of organic acid by being converted to acetyl-CoA along with the progress of the reaction, which contributes to high production efficiency.

There is no particular limit on the method of supplying acetic acid to the reaction system, and it may be added to the medium beforehand within the tolerance range of the microorganisms or continuously added to the medium along with the progress of the reaction. The acetic acid may be added to the medium after being mixed with alkali to adjust pH in accordance with the optimum pH of the medium or added in the form of acetate salt. As the acetate salt, sodium acetate, potassium acetate, ammonium acetate and the like can be suitably used. Also, not only the acetic acid artificially added in the cultivation or reaction process but the acetic acid generated as metabolic by-product of the microorganism during the cultivation can be used for the reaction, which contributes to the improvement of the material balance of the whole reaction system. Therefore, it is desirable to appropriately adjust the amount of the acetic acid to be supplied for the overall reaction, taking into consideration the amount of acetyl-CoA derived from the main material consumed in the synthesis of organic acid, the amount of acetic acid which is required as the conjugate substrate of the CoA transfer and collected as acetyl-CoA, the amount of acetic acid generated as a fermentation by-product during the cultivation process. Furthermore, it is also possible to control the acetic acid to be generated in an amount theoretically equivalent to the carbohydrate as a main material by adjusting the cultivation conditions, modifying the metabolic path of the host, and the like, so that the acetic acid is to be supplied in an amount required for the CoA transfer reaction in conjugate with acetic acid together with the artificial addition. The term "in the presence of the supplied acetic acid" as a requirement of the present invention does not only mean a case where the acetic acid is present in a status that can be detected by a generally-known method of analyzing acetic acid. That is, the term includes a case where the supplied acetic acid is present in the reaction path as a reaction intermediate to be sequentially consumed in the reaction. Such an existence form of acetic acid may be difficult to be directly detected as acetic acid, but the fact that the acetic acid is supplied and taken in the reaction path can be confirmed by conventional means such as so-called metabolic flux analysis, for example, which allows isotopically-labeled acetic acid to coexist and trace the sequential reaction product by a mass spectrometer.

EXAMPLES

The present invention is described below by referring to Examples and Comparative Examples, but the present invention is not limited thereto.

Production of 3-hydroxybutanoic acid (1)

Example 1

Production of Recombinant Microorganism

Figure 1:
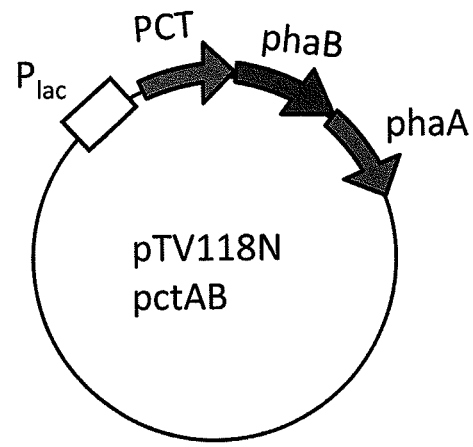
FIG. 1 is the gene mapping of plasmid pTV118NpctAB constructed in Example 1.

An about 1.6 kbp fraction of propionic acid-CoA transferase (PCT) gene was prepared from the cultured bacteria of *Megasphaera elsdenii* ATCC25940 strain (in the possession of American Type Culture Collection) by a PCR method using a primer obtained based on the previously-identified gene sequence. Similarly, from the cultured bacteria of *Ralstonia eutropha* H16 strain (in the possession of the same institute as ATCC17699), a series of gene region of about 2.3 kbp coding two enzymes of β-ketothiolase (PhaA) and acetoacetyl-CoA reductase (PhaB) derived from the same strain was obtained as a fraction including the upstream promoter-like region derived from the same strain. Upon designing the primer and cloning, the document of Taguchi et al. (PNAS, vol. 105, No. 45, P. 17323 (2008)) was referred to with respect to PCT and document of Peoples et al. (J. Biol. Chem. Vol. 264, No. 26, p. 15293-(1989)) was referred to with respect PhaA and PhaB. These fractions were inserted in the multiple cloning site of the vector plasmid pTV118N (manufactured by Takara Bio Inc.) by conventional means to construct plasmid pTV118NpctAB, which can be expressed in *Escherichia coli*. The genetic map of the plasmid is shown in FIG. 1.

*Escherichia coli* strain JM109 was transformed by conventional means using the obtained plasmid to obtain *Escherichia coli* strain transformed by the above three genes.

Example 2 and Comparative Example 1

Culture Test

After cultivating the obtained transformant on the LB agar medium containing 50 mg/l of ampicillin at 37° C. for one whole day and night, a loopful of the transformant was inoculated on 5 ml of the same liquid medium and cultivated for 12 hours.

100 μl of the obtained culture solution was transplanted to 100 ml of LB medium containing 50 mg/l of ampicillin, 20 g/l of glucose, and acetic acid in an amount molar equivalent to glucose (about 6.7 g/l) in 500 ml-volume flask and subjected to shake culture at 30° C. for 48 hours (Example 2).

Also, the culture solution was transplanted to a medium having the same composition excluding acetic acid and subjected to shake culture at 30° C. for 48 hours in a similar manner (Comparative Example 1).

The centrifuge supernatant of each of the culture products after 48 hours of cultivation was allowed to pass the sterilization filter of 0.45 μm and 10 μl of the neat liquid was subjected to HPLC under the conditions set forth below.

As a standard sample, an aqueous solution of the reagent of 3-hydroxybutanoic acid (manufactured by Sigma-Aldrich Co. LCC) in a concentration of 0.1 mass % was subjected to HPLC in a similar manner. The concentration (g/l) of 3-hydroxybutanoic acid generated in the culture solution was determined from the peak area of the culture product sample relative to that of the standard sample obtained in the same retention time.

HPLC Conditions:

column: Shodex SH-1011 (manufactured by Showa Denko K. K.)

column temperature: 60° C.

mobile phase: diluted sulfuric acid (5 mM)

flow rate: 0.6 ml/min.

detection: differential refractometer detector

The results are shown in Table 1. Improvement in the yield per carbon source input was confirmed as well as the increase in the product amount due to the addition of acetic acid.

TABLE 1

|  | Cultivation conditions | Ratio of total carbon source (glucose + acetic acid) (when the value in Comparative Example 1 is set as 1) | 3-hydroxybutanoic acid (g/l) | Product volume ratio (when the volume in Comparative Ex. 1 is set as 1) |
|---|---|---|---|---|
| Example 2 | Acetic acid is added | 1.33 | 0.6 | 2 |
| Comparative Example 1 | Acetic acid is not added | 1 | 0.3 | 1 |

Production of 3-hydroxybutanoic acid (2)

Example 3

Production of Recombinant Microorganism

Escherichia coli strain BW25113 was transformed by conventional means using plasmid pTV118NpctAB to obtain a transformed Escherichia coli strain by three genes of PhaA, PhaB and PCT.

Example 4 and Comparative Example 2

Culture Test

The transformant was cultivated in the same manner as in Example 2 and Comparative Example 1 except that the transformant prepared in Example 3 was used on a medium containing acetic acid (Example 4) and a medium without containing acetic acid (Comparative Example 2) and the concentration of 3-hydroxybutanoic acid generated in the culture solution was measured by HPLC under the same conditions.

The results are shown in Table 2. Improvement in the yield per carbon source input was confirmed as well as the increase in the product amount due to the addition of acetic acid.

TABLE 2

|  | Cultivation conditions | Ratio of total carbon source (glucose + acetic acid) (when the value in Comparative Example 2 is set as 1) | 3-hydroxybutanoic acid (g/l) | Product volume ratio (when the volume in Comparative Ex. 2 is set as 1) |
|---|---|---|---|---|
| Example 4 | Acetic acid is added | 1.33 | 3.6 | 2.3 |
| Comparative Example 2 | Acetic acid is not added | 1 | 1.6 | 1 |

Production of 3-hydroxybutanoic acid (3)

Comparative Example 3

Production of Recombinant Microorganism

Figure 2:
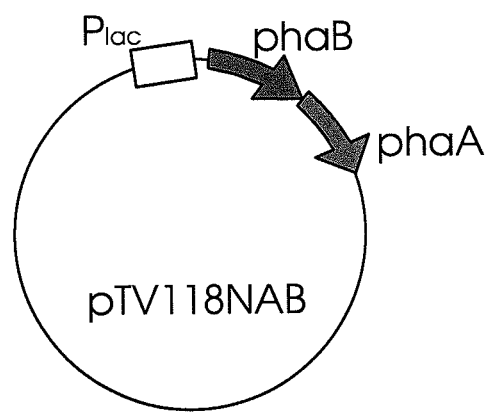
FIG. 2 is the gene mapping of plasmid pTV118NAB constructed in Comparative Example 3.

A DNA fraction of about 2.3 kbp coding two enzymes of PhaA and PhaB was inserted to the multiple cloning site of vector plasmid pTV118N to constitute plasmid pTV118NAB which can be expressed in Escherichia coli in the same way as in Example 1 except that the PCT gene fraction of Example 1 was excluded. The genetic map of the plasmid is shown in FIG. 2.

Escherichia coli strain BW25113 was transformed by conventional means using the obtained plasmid to obtain an Escherichia coli strain transformed by two genes of PhaA and PhaB.

Comparative Examples 4 to 8 and Examples 5 to 7

Culture Test

The transformants obtained in Example 3 and Comparative Example 3 were subjected to shake culture in a test tube containing 1.5 ml of LB liquid medium containing 10 g/l of glucose, acetic acid in various concentrations shown in Table 3, and 100 mg/l of ampicillin at 30° C. for 24 hours (Comparative Examples 5 to 8 and Examples 5 to 7). Untransformed Escherichia coli strain BW25113 was also cultivated in the same way (Comparative Example 4). Acetic acid which was neutralized to pH 7.0 with sodium hydrate and passed through a sterilizing filter of 0.2 μm was added to the medium.

The centrifuge supernatant of each of the culture products after 24 hours of cultivation was allowed to pass the sterilization filter of 0.2 μm and 10 μl of the neat liquid was subjected to HPLC under the conditions set forth below.

As a standard sample, an aqueous solution of the reagent of 3-hydroxybutanoic acid, acetic acid and glucose (manufactured by Sigma-Aldrich Co. LCC) in a concentration of 0.1 mass % was subjected to HPLC in a similar manner. The concentration of 3-hydroxybutanoic acid, acetic acid and glucose generated in the culture solution was determined from the peak area of the culture product sample relative to that of the standard sample obtained in the same retention time. The consumption of glucose and generation rate of 3-hydroxybutanoic acid were calculated from the obtained measurement values.

Also, OD600 and pH of the culture solution after 24 hours of cultivation were measured.

HPLC Conditions:
column: Shodex SH-1011 (manufactured by Showa Denko K. K.)
column temperature: 60° C.
mobile phase: diluted sulfuric acid (5 mM)

flow rate: 0.6 ml/min.
detection: differential refractometer detector

The results are shown in Table 3. The untransformed *Escherichia coli* sufficiently grew but 3-hydroxybutanoic acid was not generated (Comparative Example 4). *Escherichia coli* transformed by two genes of PhaA and PhaB without including PCT gene also sufficiently grew but 3-hydroxybutanoic acid was not generated either, regardless of whether acetic acid was added (Comparative Examples 5 to 7). Meanwhile, in *Escherichia coli* transformed by three genes of PhaA, PhaB and POT, 3-hydroxybutanoic acid was generated regardless of whether acetic acid was added (Comparative Example 8, Examples 5 to 7). When compared to the cultivation in the medium in which acetic acid was not added (Comparative Example 8), the production of 3-hydroxybutanoic acid showed a remarkable increase in the cultivation in the medium in which acetic acid was added (Examples 5 to 7). Also, in Examples 5 to 7, the production rate of 3-hydroxybutanoic acid remarkably increased along with an increase in the glucose consumption. It is assumed to be due to that sugar metabolism and generation of 3-hydroxybutanoic acid were enhanced by establishing a metabolic path of recycling CoA and promoting the production of 3-hydroxybutanoic acid as follows. Acetic acid added in the medium functioned as a CoA receptor, acetyl-CoA was rapidly generated by CoA transfer reaction of PCT, and 3-hydroxybutanoic acid was generated rapidly from 3-hydroxybutanoic acid-CoA in conjugate with acetyl-CoA; acetic acid generated from glucose is also recycled into acetyl-CoA by PCT; and 3-hydroxybutanoic acid is produced using the thus-generated acetyl-CoA as a substrate.

and Example 8 was sterilized by passing through a sterilizing filter of 0.2 μm, the resultant was dried in a vacuum and heated with ethanol and hydrochloric acid in chloroform according to the method of Arai Y, et al. (Plant Cell Physiol. Vol. 43, p. 555 (2002)) to obtain 3-hydroxybutanoic acid ethyl ether. The obtained ethyl ester was analyzed using GC/MS spectrometer (GCMS-QP2010 Plus; manufactured by Shimadzu Corporation) to measure $^{13}C$ contained in 3-hydroxybutanoic acid. The GC/MS chromatogram as a result is shown in FIG. 3.

3-hydroxybutanoic acid ethyl ether generates an ion fragment having m/z of 117. As is clear from FIG. 3, it was confirmed that ethyl ester derived from 3-hydroxybutanoic acid generated in the presence of acetic acid labeled with $^{13}C$ contained ion fragments having m/z of 118 and 119. That is, the acetic acid added in the medium is taken in 3-hydroxybutanoic acid and it was proved that the acetic acid added in the medium was converted to 3-hydroxybutanoic acid.

It is estimated that the ratio of the carbon derived from acetic acid in 3-hydroxybutanoic acid is 34% from the peak area ratio in each of the chromatograms. It is assumed that the rest 66% of carbon is derived from glucose. The molar concentrations of glucose consumption and 3-hydroxybutanoic acid production in Example 5 shown in Table 3 were 42 mM and 44 mM, respectively. The carbon yield from glucose to 3-hydroxybutanoic acid was about 70% and it was found that 3-hydroxybutanoic acid can be obtained from glucose at a high carbon yield.

The invention claimed is:

1. A method of producing hydroxycarboxylic acid having 3 to 6 carbon atoms, comprising biochemical synthesis of

TABLE 3

| | Transgene | Addition amount of acetic acid (g/l) | OD 600 | pH | 3-hydroxybutanoic acid (g/l) | acetic acid (g/l) | glucose consumption (g/l) | production rate of 3-hydroxybutanoic acid (g/l · hr) |
|---|---|---|---|---|---|---|---|---|
| Comparative Ex. 4 | None | 0 | 5.2 | 4.5 | Not detected | 2.6 | 2.6 | — |
| Comparative Ex. 5 | PhaA + PhaB | 0 | 5.1 | 4.6 | Not detected | 2.5 | 2.7 | — |
| Comparative Ex. 6 | PhaA + PhaB | 3.3 | 6.3 | 5.0 | Not detected | 5.3 | 2.9 | — |
| Comparative Ex. 7 | PhaA + PhaB | 6.6 | 7.8 | 5.3 | Not detected | 8.2 | 3.4 | — |
| Comparative Ex. 8 | PhaA + PhaB + PCT | 0 | 6.5 | 4.6 | 1.0 | 1.8 | 3.6 | 0.04 |
| Example 5 | PhaA + PhaB + PCT | 3.3 | 13.7 | 7.8 | 4.6 | 2.1 | 7.6 | 0.19 |
| Example 6 | PhaA + PhaB + PCT | 6.6 | 13.4 | 8.4 | 5.2 | 4.2 | 9.0 | 0.22 |
| Example 7 | PhaA + PhaB + PCT | 9.9 | 10.2 | 7.9 | 4.1 | 6.9 | 6.6 | 0.17 |

Carbon Flux Analysis

Example 8

To prove that the acetic acid added in the medium is converted to 3-hydroxybutanoic acid, the culture test was conducted in a similar manner as in Example 5 by adding the acetic acid labeled with stable isotope $^{13}C$ in the medium to measure $^{13}C$ contained in the generated 3-hydroxybutanoic acid. The concentration of 3-hydroxybutanoic acid and acetic acid after the cultivation was 4.1 g/l and 2.3 g/l, respectively, which were equal to those in Example 5 using non-labeled acetic acid. After the culture supernatant obtained by centrifuging the culture solutions of Example 5 hydroxycarboxylic acid having 3 to 6 carbon atoms-CoA using acetyl-CoA as a substrate and conducting CoA elimination reaction of hydroxycarboxylic acid having 3 to carbon atoms-CoA using CoA transferase,
in which hydroxycarboxylic acid having 3 to 6 carbon atoms is obtained by culturing transformed microorganisms which have enzyme genes that code for β-ketothiolase (PhaA), acetoacetyl-CoA reductase (PHaB), and propionic acid CoA transferase (PCT) in the presence of artificially added acetic acid and/or acetate in a medium.

2. The method of producing hydroxycarboxylic acids having 3-6 carbon atoms as claimed in claim 1, wherein said transformed microorganisms have an enzyme gene cluster for the synthesis of 3-hydroxybutyryl CoA using acetyl-CoA as a substrate and a CoA transferase gene in the presence of artificially added acetic acid and/or acetate, and wherein said hydroxycarboxylic acid having 3-6 carbon atoms is 3-hydroxybutanoic acid.

3. The method of producing hydroxycarboxylic acids having 3-6 carbon atoms as claimed in claim 1, wherein the microorganism is *Escherichia coli*, yeast, *Corynebacterium* or *Clostridium*.

4. The method of producing hydroxycarboxylic acid having 3 to 6 carbon atoms as claimed in claim 1, which comprises artificially adding the acetic acid and/or acetate to the medium after the acetic acid and/or acetate is neutralized to nearly to pH 7.

5. The method of producing hydroxycarboxylic acid having 3 to 6 carbon atoms as claimed in claim 1, which comprises continuously and artificially adding the acetic acid and/or acetate to be added artificially to the medium along with the progress of the reaction.

6. The method of producing hydroxycarboxylic acid having 3 to 6 carbon atoms as claimed in claim 4, which comprises artificially adding acetate to the medium and wherein the acetate is selected from the group consisting of sodium acetate, potassium acetate and ammonium acetate.

7. The method of producing hydroxycarboxylic acid having 3 to 6 carbon atoms as claimed in claim 5, which comprises artificially adding acetate to the medium and wherein the acetate is selected from the group consisting of sodium acetate, potassium acetate and ammonium acetate.

8. A method of producing (R)-3-hydroxybutyryl-CoA, which comprises biochemical synthesis of (R)-3-hydroxybutyryl-CoA using acetyl-CoA as a substrate and conducting CoA elimination reaction of (R)-3-hydroxybutyryl-CoA using CoA transferase, in which (R)-3-hydroxybutyryl CoA is obtained by culturing transformed microorganisms which have enzyme genes that code for β-ketothiolase (PhaA), acetoacetyl-CoA reductase (PHaB), and propionic acid-CoA transferase (PCT) in the presence of artificially added acetic acid and/or acetate.

9. A method of producing (S)-3-hydroxybutyryl-CoA, which comprises biochemical synthesis of (S)-3-hydroxybutyryl-CoA using acetyl-CoA as a substrate and conducting CoA elimination reaction of (S)-3-hydroxybutyryl-CoA using CoA transferase, in which (S)-3-hydroxybutyryl CoA is obtained by culturing transformed microorganisms which have enzyme genes that code for β-ketothiolase (PhaA), acetoacetyl-CoA reductase (PHaB), and propionic acid-CoA transferase (PCT) in the presence of artificially added acetic acid and/or acetate.

* * * * *